United States Patent [19]

Gerstenberg et al.

[11] Patent Number: 5,236,904
[45] Date of Patent: Aug. 17, 1993

[54] ERECTION-INDUCING METHODS AND COMPOSITIONS

[75] Inventors: Thomas Gerstenberg, Frederiksberg; Jan Fahrenkrug, Hellerup; Bent Ottesen, Frederiksberg, all of Denmark

[73] Assignee: Senetek, plc, St. Louis, Mo.

[21] Appl. No.: 408,754

[22] Filed: Sep. 18, 1989

[51] Int. Cl.$^5$ .................... A61K 37/00; A61K 37/02; C07K 5/00; C07K 4/00
[52] U.S. Cl. ........................................ 514/12; 530/324
[58] Field of Search ........................... 514/12; 530/324

[56] References Cited

U.S. PATENT DOCUMENTS

| | | | |
|---|---|---|---|
| 3,898,329 | 8/1975 | Said et al. | 424/177 |
| 4,757,133 | 6/1988 | Ito et al. | 530/324 |
| 4,939,224 | 3/1990 | Musso et al. | 530/324 |

FOREIGN PATENT DOCUMENTS 0354992  2/1990  European Pat. Off.

OTHER PUBLICATIONS

Polak et al., Peptides, vol. 5, 1984 pp. 225–230.
Bodner et al., PNAS, vol. 82, 1985, pp. 3548–3551.
Willis et al., Chemical Abstracts, vol. 96, 1982, No. 4180p.
Kiely et al., Biological Abstracts, vol. 88, 1989, No. 123539.
Ottesen et al., Chemical Abstracts, vol. 100, 1984, No. 97098g.
Fahrenkrug et al., Annals of New York Academy of Sciences, vol. 527, 1988, pp. 393–404.
Ottesen, et al., "Vasoactive intestinal polypeptide (VIP) increases vaginal blood flow and inhibits uterine smooth muscle activity in women," *Euro. Journal of Clinical Investigation* 13:321–324 (1983).
Wagner, et al., "Intracavernosal injection of vasoactive intestinal polypeptide (VIP) does not induce erection in man per se," *World Journal Urol.*, 5:171–172 (1987).
Kiely, et al., "Penile response to intracavernosal vasoactive intestinal polypeptide alone and in combination with other vasoactive agents," *British Journal of Urology*, 64:191–194 (1989).
Brindley, "Cavernosal alpha-blockade: a new technique for investigating and treating erectile impotence," *British Journal Psychiat.* 143:332–337 (1983).
Willis, et al., "Vasoactive intestinal polypeptide (VIP) as a putative neurotransmitter in penile erection," *Life Sciences*, 33:383–391 (1983).

(List continued on next page.)

Primary Examiner—Merrell C. Cashion, Jr.
Assistant Examiner—A. M. Davenport
Attorney, Agent, or Firm—Fitch, Even, Tabin & Flannery

[57] ABSTRACT

The present invention provides methods and compositions for inducing penile erections, sufficient for vaginal penetration, in a human male suffering from impotence. When the impotence is substantially only neurogenic, psycogenic or neurogenic and psychogenic, a method of the invention comprises (A) administering to the male by intracavernosal injection peptide N-terminal histidine C-terminal methionineamide and (B) sexually stimulating the male. When the impotence is caused by severe atherosclerosis, a method of the invention comprises (A) administering to the male by intracavernosal injection an amount of a physiologically acceptable composition comprising (1) a neuropeptide selected from the group consisting of human vasoactive intestinal peptide and peptide N-terminal histidine C-terminal methionineamide and (2) an alpha-adrenergic blocker, such as phentolamine or prazosin, and (B) sexually stimulating the male. The invention also entails a physiologically acceptable composition suitable for use in inducing, upon administration by intracavernosal injection, an erection, sufficient for vaginal penetration, in a human male suffering from impotence, which is caused by severe atherosclerosis, which composition comprises (1) a neuropeptide selected from the group consisting of vasoactive intestinal peptide and peptide N-terminal histidine C-terminal methionineamide and (2) an alpha-adrenergic blocker, such as phentolamine or prazosin.

21 Claims, No Drawings

OTHER PUBLICATIONS

Ottesen, et al., "Penile erection: possible role for vasoactive intestinal polypeptide as a neurotransmitter," *British Medical Journal,* 288:9–11 (1984).

Adaikan, et al., "Is vasoactive intestinal polypeptide the principal transmitter involved in human penile erection?" *The Journal of Urology,* 135:638–640 (1986).

Itoh, et al., "Human preprovasoactive intestinal polypeptide contains a novel PHI-27-like peptide, PHM-27," *Nature,* 304:547–549 (1983).

Weiner, "Drugs that inhibit adrenergic nerves and block adrenergic receptors", in Goodman and Gilman, eds., *The Pharmacological Basis of Therapeutics,* MacMillan Publishing Co., New York, N.Y., 6th Ed., Chapter 9:176–210 (1980).

ERECTION-INDUCING METHODS AND COMPOSITIONS

TECHNICAL FIELD

The present invention concerns methods and compositions for inducing penile erections in human males suffering from impotence.

BACKGROUND OF THE INVENTION

Erectile insufficiency, to the extent that vaginal penetration is not possible, commonly referred to as "impotence," is thought to affect about 12% of adult men under age 45, about 20% of men at age 60, and about 55% of men at age 75.

A number of causes of erectile insufficiency, other than anatomical deficiencies of the penis or scrotum which preclude an erection sufficient for vaginal penetration, have been identified. Thus, in some males, the erectile dysfunction is psychological (due to, e.g., anxiety or depression) with no apparent somatic or organic impairment; such erectile dysfunction is referred to as "psychogenic." About 15%-20% of cases of impotence are psychogenic.

In other cases, the erectile dysfunction is associated with atherosclerosis of the arteries supplying blood to the penis; such dysfunction is referred to as "arteriogenic" or "atherosclerotic." About 40%-60% of cases of impotence are arteriogenic.

In still other cases, where the dysfunction is referred to as "venous leakage," or "abnormal drainage," there is leakage from veins in the penis such that sufficient pressure for an erection can be neither obtained nor maintained, particularly if, in addition, as commonly observed, there is also some arteriogenic dysfunction whereby supply of blood to the penis is impaired.

In still other cases, the dysfunction is associated with a neuropathy, or due to nerve damage arising from, e.g., surgery or a pelvic injury, in the nervous system affecting the penis; such a dysfunction is referred to as "neurogenic." About 10%-15% of cases of impotence are neurogenic.

Because of the high incidence of erectile insufficiency among diabetics, particularly those with insulin-dependent diabetes mellitus, erectile dysfunction in diabetics is often classified as "diabetogenic," although the underlying dysfunction is usually neurogenic associated with neuropathy but may be arteriogenic or both neurogenic and arteriogenic. About half of diabetic males suffer from erectile insufficiency, and about half of the cases of neurogenic impotence are in diabetics.

Further, erectile insufficiency is sometimes a side effect of certain drugs, such as beta-blockers, administered to reduce blood pressure in persons suffering from hypertension, or drugs to treat depression or anxiety. Excessive alcohol consumption has also been linked to erectile insufficiency. These forms of erectile insufficiency may be regarded as a subset of neurogenic or psychogenic insufficiency.

In any individual suffering from impotence, there may be more than one cause of erectile dysfunction.

A number of methods to cure or treat impotence are known. In cases of psychogenic dysfunction, psychological counseling is sometimes effective to cure the dysfunction. A case of psychogenic impotence often can be cured by counseling coupled with demonstrating to the patient that he is capable of having a full erection by inducing such an erection one or a few times in the patient.

Insufficiency due to excessive alcohol consumption is sometimes cured by reducing or eliminating such consumption.

In the rare cases where the insufficiency is untreatable on account of venous leakage, surgery can usually be employed to repair the venous lesion and thereby either cure the insufficiency or, if there remains an erectile insufficiency after repair of the venous lesion, render the insufficiency treatable by a pharmacological method, such as that of the present invention.

In some cases, particularly where the dysfunction is psychogenic or neurogenic and severe atherosclerosis is not involved, injection of papaverine, a smooth muscle relaxant, or phenoxybenzamine, a non-specific blocker and hypotensive, into a corpus cavernosum has been found to cause an erection sufficient for vaginal penetration. Papaverine is now widely used to treat impotence, although papaverine is ineffective in overcoming impotence due, at least in part, to severe atherosclerosis.

Also in cases where severe atherosclerosis is not a cause of the dysfunction, intracavernosal injection of phentolamine, an alpha-adrenergic blocker, causes an erection sufficient for vaginal penetration, but one of significantly shorter duration than one caused by intracavernosal injection of papaverine or phenoxybenzamine and of such short duration that satisfactory sexual relations are difficult or impossible.

Also widely used to treat impotence are penile implants, whereby an erection sufficient for vaginal penetration can be caused mechanically. In recent years, implants have been employed especially in cases where injections of papaverine are ineffective, which are usually cases of severe atherogenic impotence.

The neuropeptide, human vasoactive intestinal peptide (hereinafter referred to as "VIP"), is thought to be associated with erections in normal males (i.e., males not suffering from erectile insufficiency). Injection of up to 20 μg of VIP (at 20 μg/ml of diluent) into a corpus cavernosum of a normal male, without subjecting the male to sexual stimulation, causes only slight swelling (slight tumescence) of the penis but not an erection. However, when coupled with visual sexual stimulation, sexual stimulation by vibration, or both types of stimulation, as little as 1 μg of the neuropeptide (at 1 μg/ml of diluent) injected into a corpus cavernosum of a normal male facilitates full erection. See Wagner and Gerstenberg, World J. Urol. 5, 171-172 (1987). Prior to the present invention, doses of VIP that, on one hand, are adequate (when coupled with sexual stimulation) to induce erections in males suffering from impotence but that, on the other hand, minimize or avoid systemic side effects due to administration of VIP (such as flushing of the skin and hypotension) were not identified. It is known that VIP alone, coupled with sexual stimulation, does not induce erections in males who are impotent due to severe atherosclerosis.

The human neuropeptide, peptide N-terminal histidine C-terminal methionineamide (hereinafter referred to as "PHM"), has not, prior to the present invention, been identified as a substance that, together with sexual stimulation, is capable of inducing erections.

Treatment of impotence with papaverine or phenoxybenzamine often results in priapism, a locking-up of an erection for a long period of time, typically a few hours and sometimes longer than 24 hours. Priapism is a serious, deleterious side effect of treatment of erectile insufficiency with these drugs. Beyond the embarrassment that may be caused for some men, priapism is usually painful, irreversibly damages erectile tissue, and, to be relieved, requires bleeding or pharmacological intervention (e.g., injection of a sympathomimetic drug such as adrenaline). Even if priapism does not occur with use of papaverine, such use is associated with a painful, burning sensation in the first two or so minutes after the injection and there are indications that repeated use of papaverine causes undesirable, extensive intracavernous fibrosis. Further, as indicated above, impotence arising from severe atherosclerosis is not susceptible to treatment with papaverine, phenoxybenzamine, phentolamine or papaverine together with phentolamine.

In any case, phenoxybenzamine is not suitable for use in treating impotence because of the drug's carcinogenicity.

Treatment of impotence with penile implants also entails serious disadvantages. Such treatment requires surgery and entails total destruction of the erectile tissues of the penis, forever precluding normal erection.

SUMMARY OF THE INVENTION

It has now been found surprisingly that PHM, upon intracavernosal injection coupled with sexual stimulation, induces erections in males suffering from impotence that is not caused by severe atherosclerosis.

Further, it has been found unexpectedly that impotence, which is caused by severe atherosclerosis, can be treated effectively by intracavernosal injection of VIP or PHM in combination with an alpha-adrenergic blocker, such as phentolamine or prazosin, and coupled with sexual stimulation.

Induction of an erection with VIP or PHM in accordance with the invention advantageously does not entail priapism or the burning pain associated with such induction with papaverine.

Further, intracavernosal injection of either or both of VIP and PHM in combination with an alpha-adrenergic blocker provides the first effective, non-surgical method for inducing erections in males suffering from impotence due to severe atherosclerosis. This method of the invention advantageously avoids the surgery necessary for, and the tissue destruction caused by, penile implants, the only effective means known heretofore for treating severely atherosclerotic impotence.

DETAILED DESCRIPTION OF THE INVENTION

In one of its aspects, the invention entails a method of inducing an erection in a human male suffering from impotence, which is substantially only neurogenic or psychogenic, which method comprises (A) administering to the male by intracavernosal injection a physiologically acceptable composition which comprises an erection-inducing-effective amount of PHM, and (B) sexually stimulating the male.

In another of its aspects, the invention encompasses a method of inducing an erection in a human male suffering from impotence, of which severe atherosclerosis is a cause, which method comprises (A) administering to the male by intracavernosal injection a physiologically acceptable composition which comprises (i) a neuropeptide selected from the group consisting of VIP and PHM and (ii) an alpha-adrenergic blocker; and (B) sexually stimulating the male.

In still another aspect, the invention entails a composition which is effective to induce an erection in a human male, suffering from impotence of which severe atherosclerosis is a cause, upon (A) administration of the composition by intracavernosal injection to said male and (B) sexual stimulation of said male, which composition is physiologically acceptable for administration to a human male by intracavernosal injection and comprises (i) a neuropeptide selected from the group consisting of VIP and PHM and (ii) an alpha-adrenergic blocker.

By reference herein to impotence which is "substantially only neurogenic or psychogenic" is meant impotence which is substantially only neurogenic, psychogenic or both neurogenic and psychogenic. This, in turn, means impotence which is not due to an anatomical deficiency which precludes an erection sufficient for vaginal penetration (e.g., lack of a penis or a substantial portion thereof), and which is not untreatable on account of venous leakage or due to severe or untreatable atherosclerosis. Determination whether a human male is suffering from impotence which is substantially only neurogenic or psychogenic is readily made by a person ordinarily skilled in the art using a number of readily available diagnostic procedures. Thus, a male suffering from impotence can first be given a physical examination with particular attention to possible penile and scrotal pathology, whereby any anatomical deficiency precluding an erection sufficient for vaginal penetration can be detected, and then, in the absence of such an anatomical deficiency, can be subjected to tests, whereby penile venous leakage or severe or untreatable atherosclerosis can be detected.

Such tests include determination of the penobrachial blood pressure index (PBPI)), Doppler investigation of the penile arteries, and a papaverine test.

The PBPI is the penile systolic blood pressure divided by the systolic blood pressure determined at one of the arms. These blood pressures can be determined by any of numerous standard techniques. Thus, the penile systolic blood pressure can be determined by placing, around the base of the free part of the penis in the flaccid state, an inflatable cuff, which is capable of being used to apply variable pressure, readable from a gauge, to an object around which the cuff is placed, localizing the penile arteries with a Doppler ultrasound probe (e.g., an 8 MHz probe, such as the Mini Doplex D500 TM available from Huntleigh Technology, Luton, United Kingdom), and then inflating and deflating the cuff and ascertaining the pressure at which the Doppler sound reappears. The pressure at which the Doppler sound reappears is the penile systolic blood pressure. A male's penile blood pressure is regarded as normal if his PBPI is >0.80.

With regard to Doppler investigation, each of the two penile cavernous arteries is investigated distal to the aforementioned cuff using the Doppler ultrasound probe. The function of each of the two arteries is assessed by Doppler ultrasound using an arbitrary scale of 0, 1, 2 or 3, where 0 means that the function is so deficient that the artery cannot be located and 3 means that the artery is well enough that maximal Doppler sound is observed.

In the papaverine test, a tourniquet is placed at the base of the free part of the penis and tightened and then, with the patient seated, 30 mg of papaverine in 1 ml of a physiologically acceptable fluid such as physiological saline or phosphate-buffered saline is injected into the penile cavernous body. (In persons suspected of having impotence due to a suprasacral nerve lesion or a psychogenic dysfunction, only 15 mg of papaverine is administered, because of the high incidence of papaverine-induced priapism in such cases.) Five minutes after the injection, the tourniquet is removed and an ultrasound Doppler investigation of the penile cavernous arteries is carried out as described above. The function of the arteries is regarded as normal if both of them score a 3 on the arbitrary scale. After the Doppler investigation, penile vibration, at about 40 Hz with an amplitude of about 1.2 mm (carried out with, e.g., a Vibrector TM, from Multicept, Gentofte, Denmark) is carried out for five to ten minutes and then erectile response is evaluated. Erectile response is classified as full rigidity, if the angle between the penis and the legs in the standing position is >90°, half rigidity if said angle is >45° but less than or equal to 90°, and tumescence or no response if said angle is less than or equal to 45°.

The papaverine employed in the "papaverine test" described above could be replaced with VIP (approximately 50 μg) or, based on a discovery underlying the present invention, PHM (approximately 50 μg).

An impotent male, who does not have an anatomical deficiency which would preclude having an erection sufficient for vaginal penetration, who has a PBPI >0.80, who has scores of 2 or 3 in Doppler ultrasound investigations of both of the cavernous arteries of the penis after papaverine injection as described above, and who has a fully rigid erection after papaverine injection and vibration as described above, is suffering from impotence which is "substantially only neurogenic or psychogenic", as that phrase is employed in the present specification. It is possible that atherosclerosis or venous leakage contributes to such impotence, and atherosclerosis likely does contribute if the score is less than 3 in the Doppler investigation of one or both of the cavernous arteries after papaverine injection; but any venous leakage or atherosclerosis in such impotence is not untreatable and, consequently, is not a "substantial" factor in the impotence and such atherosclerosis, if any, is less than "severe" (as the term "severe atherosclerosis" is employed herein).

Impotence, which is a side-effect of drugs, such as beta-blockers, is deemed to be neurogenic impotence in the present specification. Similarly, impotence, which is a result of alcoholism or excessive consumption of alcohol, is deemed to be neurogenic or psychogenic impotence, for purposes of the present specification. Thus, a male who is diagnosed in accordance with the present specification as suffering from impotence, which is "substantially only neurogenic or psychogenic", as that phrase is employed in the present specification, is regarded, for purposes of the present specification, as suffering from impotence, which is substantially only neurogenic, psychogenic or both neurogenic and psychogenic, even though an underlying cause of the impotence has been identified as a side-effect of a drug, alcoholism or excessive consumption of alcohol.

Reference herein to impotence, "of which severe atherosclerosis is a cause", is meant impotence which is caused, at least in part, by "severe" atherosclerosis but is not associated with an anatomical deficiency, which would preclude an erection sufficient for vaginal penetration, is not untreatable on account of venous leakage, and, although it can be contributed to by neurological or psychological factors, is not "substantially only neurogenic or psychogenic", within the meaning of that phrase in the present specification.

In the present specification, "severe" atherosclerosis is differentiated from "untreatable" atherosclerosis. In untreatable atherosclerosis, the arteries of the penis are so severely blocked that treating impotence pharmacologically could not be effective in inducing an erection sufficient for vaginal penetration. Generally, a male with a PBPI less than about 0.60, with scores of 0 in Doppler investigations of both penile cavernous arteries (after papaverine injection as described above), and with a less than fully rigid erection after papaverine injection and vibration will have impotence caused by "untreatable" atherosclerosis.

Reference in the present specification to impotence that is due to "untreatable" venous leakage means impotence that, due to venous leakage, cannot be effectively treated pharmacologically, although it might be correctable by repairing the venous leakage surgically. Methods are available to ascertain whether impotence is untreatable on account of venous leakage. One method of ascertaining whether untreatable venous leakage is a cause of impotence is by cavernosometry, optionally supplemented with cavernosography. See, e.g., Delcour et al., Radiology 161, 799 (1986); Porst et al., J. Urol. 137, 1163 (1987); Lue et al., J. Urol. 137, 829 (1987). Cavernosometry can be done using, both before and after intracavernosal injection of 60 mg of papaverine (in 1 ml of physiological saline), infusion of physiological saline through a 19-gauge needle into one corpus cavernosum with a 21-gauge needle inserted into the other corpus cavernosum for measurement of intracorporal pressure (which is recorded on a plotter). The infusion rates needed to induce and maintain an erection are measured. If the infusion rate needed to maintain an erection is greater than 50 ml/min before administration of the papaverine and greater than 15 ml/min after administration of the papaverine, untreatable venous leakage is present. As long as an erection can be achieved at some flow rate less than about 100 ml/min before injection of the papaverine and less than about 50 ml/min after the injection of papaverine, it might be possible, using cavernosography, to locate the venous lesion associated with the leakage, and thereby confirm the diagnosis based on cavernosometry and provide information for possible surgical correction of the leakage. In the cavernosography, the penis is X-rayed, both before and after intracavernosal injection of 60 mg papaverine (in 1 ml of physiological saline), while infusing contrast medium into the corpus cavernosum (e.g., through a 19-gauge needle) at a flow rate that maintains an erection during the x-raying. Numerous contrast media suitable for the procedure are available in the art; these are typically aqueous solutions of iodinated compounds that provide between about 180 mg/ml and about 360 mg/ml of iodine. Examples are Omnipaque 240 TM, which is a solution of iohexol providing 240 mg/ml of iodine sold by Winthrop Pharmaceuticals, New York, N.Y., USA, and Iopamiro ®, which is a solution of iopamidol providing 300 mg/ml iodine sold by Astra Meditec, Goteborg, Sweden. Typically 50–100 ml of the contrast medium will be employed for each x-ray (i.e., before and then after the injection of papaverine). In the cavernosometry and cavernosography, 30 mg papaverine (in 1 ml physiological saline) coupled with stimulation by vibration can be employed in place of 60 mg papaverine (in 1 ml physiological saline).

Reference herein to "intracavernosal" injection is to injection into either corpus cavernosum of the penis.

Such injection is carried out by any conventional injection means (e.g., employing an hypodermic syringe and needle or a similar device such as the NovolinPen TM sold by Squibb-Novo, Inc., Princeton, N.J., USA) by the male carrying out the injection on himself or by another person (such as a partner during sexual relations or a physician) carrying out the injection on the male whose erection is to be induced.

A single dose, with active ingredients in sufficient quantity to induce an erection, is administered as a bolus into the cavernous body. Preferably a thin (e.g., 26-gauge to 28-gauge) and short (10 mm to 13 mm) hypodermic needle is employed. Typically, a 12 mm, 27-gauge needle is employed.

"VIP" means human vasoactive intestinal peptide, a known, 28-amino acid, carboxy-terminal amidated neuropeptide. "PHM" means peptide N-terminal histidine C-terminal methionineamide, a known, 27-amino acid, carboxy-terminal amidated, human neuropeptide. See Itoh et al., Nature 304, 547-549 (1983). Reference to a mass of VIP or PHM in a composition is to the mass of the polypeptide rather than that of the acid addition salt of the polypeptide, in case the composition were prepared with such a salt of the polypeptide.

Numerous compounds are known in the pharmacological arts to be alpha-adrenergic blockers and all of these compounds are comprehended by the term "alpha-adrenergic blocker" as used in the present specification. See, e.g., Weiner, "Drugs that Inhibit Adrenergic Nerves and Block Adrenergic Receptors," in Goodman and Gilman, eds., The Pharmacological Basis of Therapeutics," MacMillan Publishing Co., New York, N.Y., USA, 6th Ed., p. 179 (1980). Alpha-adrenergic blockers include, among others, phentolamine and prazosin. Preferred forms of phentolamine for use in accordance with the invention are phentolamine chloride and phentolamine mesylate. A preferred form of prazosin for use in accordance with the invention is prazosin chloride. Unless otherwise noted, reference in this specification to a mass of an alpha-adrenergic blocker in a composition is to the mass that the blocker would have in the composition if all of the blocker were present as the chloride salt.

By a "physiologically acceptable composition" in the present specification is meant an aqueous solution that is physiologically acceptable for administration by intracavernosal injection into the penis. Thus, in addition to water, VIP or PHM (or both) and, possibly also, alpha-adrenergic blocker(s), such a composition can include physiologically acceptable buffers, salts, preservatives and the like at physiologically acceptable concentrations. The physiologically acceptable compositions will preferably be sterile at the time of administration by intracavernosal injection. Among the physiologically acceptable compositions for use in the methods of the invention is physiological saline or phosphate buffered saline, in which VIP or PHM or both (optionally in the form of non-toxic salt(s)) and possibly also an alpha-adrenergic blocker (also optionally in the form of a non-toxic salt) are dissolved. Such a physiologically acceptable composition in accordance with the invention can also include a non-irritant preservative, such as, e.g., benzalkonium chloride at 0.05% (w/v) to 0.2% (w/v). As the skilled will understand, there are numerous non-toxic salts of VIP, PHM and alpha-adrenergic blockers that can be employed in a physiologically acceptable composition for use in the methods of the invention, including, among others, the chloride, bromide, acetate, sulfate, and mesylate salts.

Use in the present specification of the term "consisting essentially of" in connection with a substance which is part of a composition means that the substance is the only one in the composition that is pharmacologically active in inducing an erection but that other substances, such as water, buffers, salts, preservatives and the like, which are not pharmacologically active in inducing an erection, may be present in the composition.

Methods of preparing compositions for use in the methods according to the invention will be readily apparent to the skilled. Thus, the sterile, pharmacologically active substances (VIP or PHM, alpha-adrenergic blocker) simply are dissolved to the desired concentration in the sterile aqueous solution, which consists of the other substances of the composition being prepared. The peptide or peptides, and the alpha-adrenergic blocker, if any, of a composition can be combined with the aqueous solution to make the composition immediately prior to administration thereof or at any desirable time prior to administration thereof. However, because of the lability of phentolamine in solution, a composition which comprises phentolamine should be prepared by adding the phentolamine (or salt thereof) immediately prior to administration of the composition. If a composition is prepared more than a few hours prior to the time it is used, the composition will desirably include a preservative, such as a benzalkonium salt, cresol, or the like, as understood in the art, and will preferably be held at a temperature between about 0° C. and about 5° C. until use.

Desirably, a single dose of a composition employed in a method of the invention has a volume between about 0.1 ml and about 5 ml, and preferably about 1 ml. Thus, the concentrations of peptide(s) and blocker (if any) in such a composition desirably are set to place the volume of a single dose, with the intended quantities of peptide(s) and blocker (if any) for the dose, within such range of about 0.1 ml to about 5 ml. As indicated above, an erection is induced by a single dose of a composition of the invention.

Sexual stimulation, as part of a method according to the invention, is any form of sexual stimulation that would induce an erection in a normal male who is not suffering from erectile insufficiency. The sexual stimulation can be that which occurs in the course of sexual relations between the male, whose erection is to be induced in accordance with the invention, and another person or can be outside sexual relations with another person. Examples of methods of sexual stimulation include, alone or in combination, touching or erotically manipulating erogenous areas of the genital organs or other erogenous parts of the body; providing visual stimulation, as with a pornographic film or other form of sexually stimulative show or display; or providing vibratory stimulation to the penis, at between about 30 Hz and about 100 Hz with an amplitude of about 1 mm to about 5 mm, as can be provided, for example, by resting the penis on the table of a vibrating apparatus such as that of a Vibrector system (Multicept, Gentofte, Denmark). In inducing an erection in an impotent male outside of sexual relations, as, for example, in a physician's inducing an erection in a patient suffering from psychogenic impotence, a preferred method of sexual stimulation includes providing visual stimulation, as with a pornographic film, simultaneously with vibratory stimulation of the penis, as with a Vibrector system set to between about 30 Hz and about 60 Hz (usually about 50 Hz) in frequency and between about 1 mm and about 2.5 mm (usually about 2.2 mm) in amplitude.

The sexual stimulation can begin before or after the intracavernosal injection in accordance with the invention. If the stimulation begins after said injection, it is preferably begun within 5 to 10 minutes to insure that there is significant overlap of the pharmacological effects of the neuropeptide(s) and alpha-adrenergic blocker(s), if any, in the composition administered by the injection in accordance with the invention and the stimulative effects of the sexual stimulation. Whether the stimulation begins before or after the injection, it will continue preferably at least until an erection sufficient for vaginal penetration is achieved.

In carrying out the methods of the invention, it is preferred that, for a period of time between about 1 minute and about 15 minutes (preferably about 5 minutes–10 minutes), the penis be constricted near the base thereof and between said base and the point at which the injection into a corpus cavernosum occurs, in order to limit loss of injected fluid from the corpa cavernosum before the ingredients in the fluid, that are active in inducing erection, have been able to have erection-inducing effects. The constriction can be effected by any means known in the art, such as with a tourniquet, cuff, rubber band or the like, or even manually, in order to slow the release of the injected fluid and the pharmacologically active substance(s) therein into the general circulation.

It is contemplated that the compositions of the invention will be used, and the methods of the invention will be carried out, under the guidance of a physician.

The dose of VIP or PHM, and alpha-adrenergic blocker (if any), most suitable to induce an erection sufficient for vaginal penetration in a male suffering from impotence will vary somewhat depending on the dysfunction(s) underlying the impotence, the age, the general medical condition, and the condition of the cardiovascular system of the male, and whether the male is being treated with drugs, such as beta-blockers, that may impair erectile sufficiency. In any case, a skilled physician will be able to determine readily a suitable dose of VIP or PHM, and a suitable dose of an alpha-adrenergic blocker, if any, to be administered together with the VIP or PHM to induce an erection in a male in accordance with the present invention.

A dose of PHM in the range of between about 10–15 $\mu$g and about 45–50 $\mu$g, and most preferably about 30 $\mu$g, is superior for inducing an erection in a male suffering from impotence, which is substantially only neurogenic or psychogenic. On the one hand, when coupled with sexual stimulation, virtually all males suffering from such impotence will achieve an erection sufficient for vaginal penetration with intracavernosal injection of a dose of 30 $\mu$g in a physiologically acceptable diluent, and many will achieve such an erection with a dose as low as 10 $\mu$g. On the other hand, there appears to be no advantage in administering more than about 60 $\mu$g.

Unexpectedly, PHM is found to have a somewhat longer lasting pharmocological effect than VIP at the same dosage. Thus, it can be expected that PHM can be used at a lower dosage than VIP to achieve the same effect as VIP and, consequently, that the magnitude of side-effects (hypotension, increased pulse rate, flushing of the face and trunk) often observed when high doses (greater than about 40 $\mu$g) of VIP are used to induce an erection can be reduced when PHM is used in place of VIP by using the PHM at a lower dosage.

A dosage volume of about 1 ml has been found to be convenient.

A preferred composition for carrying out the method of the invention to effect an erection in a male suffering from impotence, which is substantially only neurogenic or psychogenic, is a solution of PHM at 30 $\mu$g/ml in physiological saline, with the PHM being the only substance in the solution that is pharmacologically active in inducing an erection. Preferably 1 ml of the preferred composition is administered as a bolus by injection into a corpus cavernosum while the penis is constricted at its base with a tourniquet. About 5–10 minutes after the injection, the tourniquet is released and, if not already started before the tourniquet is released, sexual stimulation is begun. An erection sufficient for vaginal penetration is then achieved typically within 5 minutes. Priapism does not occur.

VIP, PHM or mixtures of VIP and PHM alone are not effective to induce erections in males suffering from impotence, of which severe atherosclerosis is a cause. However, coupled with sexual stimulation, administration by intracavernosal injection of one of the neuropeptides (or a mixture of both) together with an alpha-adrenergic blocking agent is effective to induce an erection sufficient for vaginal penetration in a male suffering from impotence, of which severe atherosclerosis is a cause.

In inducing an erection, in accordance with the invention, in a male suffering from impotence, of which severe atherosclerosis is a cause, essentially the same steps are followed as with using, in accordance with the invention, PHM to induce an erection in a male suffering from impotence, which is substantially only neurogenic or psychogenic. Thus, between about 0.1 ml and about 5 ml, and preferably about 1 ml, of a physiologically acceptable composition comprising one of VIP or PHM or a mixture thereof and an alpha-adrenergic blocker is administered as a bolus by intracavernosal injection during, or prior to the initiation of, sexual stimulation and preferably with the penis constricted at its base for between about 1 minute and about 15 minutes (preferably about 5 minutes–about 10 minutes) after the injection.

In a composition of the invention, for use in the method of the invention for inducing an erection in a male suffering from impotence, of which severe atherosclerosis is a cause, VIP and PHM together will be present at a concentration such that, upon the intracavernosal injection of a predetermined volume of the composition to induce an erection, between about 10 $\mu$g and about 100 $\mu$g, and more preferably between about 20 $\mu$g and about 70 $\mu$g, of neuropeptide will be administered. To minimize side-effects when VIP is employed in such a composition, it is preferred that less than about 60 $\mu$g of VIP be administered. In most cases, it is found that 30 $\mu$g of VIP or PHM (together with alpha-adrenergic blocker) is sufficient to induce an erection sufficient for vaginal penetration in a male suffering from impotence, of which sever atherosclerosis is a cause. Thus, typical compositions according to the invention, of which 1 ml would be administered by intracavernosal injection to induce an erection in a male suffering from impotence, of which severe atherosclerosis is a cause, will comprise between about 10 $\mu$g/ml and about 100 $\mu$g/ml, and more preferably about 30 $\mu$g/ml, of VIP or PHM (or both VIP and PHM together) together with alpha-adrenergic blocker in physiological saline.

The concentration of alpha-adrenergic blocker in such a composition will depend on the severity of the atherosclerosis, the potency of the blocker, and on the volume of composition that is to be administered to induce an erection. With phentolamine, the concentration should be adjusted such that between about 50 μg and 5,000 μg (and preferably about 2,000 μg) are administered to induce an erection. With prazosin, the concentration should be adjusted such that between about 5 μg and about 1,500 μg (and typically about 100 μg) are administered. The skilled will readily understand, from the relative potencies of alpha-adrenergic blockers in reducing hypertension, the doses of phentolamine and prazosin required, if the two are used in combination in a composition of the invention, and the dose of any other alpha-adrenergic blocker (alone or in combinations with others) required to induce an erection according to the invention in a male suffering from impotence, of which severe athero-sclerosis is a cause. Of course, from the known doses, concentrations in compositions according to the invention are readily determined.

Three combinations of VIP with phentolamine have been found to be effective in inducing erections in males suffering from impotence of which severe atherosclerosis is a cause: 30 μg VIP with 500 μg phentolamine, 30 μg VIP with 1,000 μg phentolamine, and 30 μg VIP with 2,000 μg phentolamine.

All volumes and volume-dependent concentrations recited herein are intended to be at 25° C.

While the invention has been described herein with some specificity, the skilled will appreciate variations and modifications of what has been described that are within the spirit of the invention as described and claimed. It is intended that such variations and modifications be encompassed by the following claims.

What is claimed is:

1. A method of inducing an erection in a human male suffering from impotence, comprising:
   (A) administering to said male by intracavernosal injection an erection-inducing-effective amount of peptide histidine methionine (PHM) or vasoactive intestinal peptide (VIP) in a physiologically acceptable solution; and
   (B) sexually stimulating said male, wherein:
   the amount of PHM or VIP is effective in the absence of any other erection-inducing compounds to induce an erection sufficient for vaginal penetration in the presence of sexual stimulation in said male; and
   said impotence is substantially neurogenic or psychogenic impotence.

2. The method of claim 1, wherein the volume of the physiologically acceptable solution administered to the male is between 0.1 ml and 5 ml and the amount of PHM administered is between 10 μg and 60 μg.

3. A method of inducing an erection sufficient for vaginal penetration in a human male suffering from impotence, comprising:
   (A) administering to said male by intracavernosal injection a physiologically acceptable composition containing
      (i) between 15 μg and 60 μg of a neuropeptide selected from the group consisting of vasoactive intestinal peptide (VIP) and peptide histidine methionine (PHM) and (ii) an alpha-adrenergic blocker, at a dose effective to induce such an erection when administered with said neuropeptide; and
   (B) sexually stimulating said male.

4. The method of claim 3, wherein said neuropeptide is VIP.

5. The method of claim 3, wherein said neuropeptide is PHM.

6. The method of claim 4, wherein the volume of said injected, physiologically acceptable composition is between 0.1 ml and 5 ml, inclusive, and said alpha-adrenergic blocker is selected from the group consisting of phentolamine, at a dose between 0.1 mg and 5 mg, inclusive, and prazosin, at a dose between 0.01 mg and 1 mg, inclusive.

7. The method of claim 5, wherein the volume of said injected, physiologically acceptable composition is between 0.1 ml and 5 ml, inclusive, and said alpha-adrenergic blocker is selected from the group consisting of phentolamine, at a dose between 0.1 mg and 5 mg, inclusive, and prazosin, at a dose between 0.01 mg and 1 mg, inclusive.

8. The method of claim 6, wherein said alpha-adrenergic blocker is phentolamine.

9. The method of claim 7, wherein said alpha-adrenergic blocker is phentolamine.

10. A method according to any one of claims 1-9 wherein, for between 1 minute and 10 minutes after the injection, the penis of the male is constricted between the base thereof and the point on the penis at which the injection occurred.

11. A method according to claim 10 wherein the sexual stimulation of the male is sexual stimulation in the course of sexual relations between said male and another person.

12. A method according to claim 10 wherein the sexual stimulation of the male is by penile vibration simultaneously with visual sexual stimulation.

13. A composition formulated as a single dose that is physiologically acceptable for administration to a human male by intracavernosal injection, comprising:
   (i) a neuropeptide selected from the group consisting of vasoactive intestinal peptide (VIP) and peptide histidine methionine (PHM), and
   (ii) an alpha-adrenergic blocker, wherein:
   the amounts of said neuropeptide and blocker are, with sexual stimulation, effective, in the absence of other erection-inducing substances to induce an erection when administered together by intracavernosal injection to a human male suffering from impotence:
   administration of a single dose of the composition does not cause priapism in a male treated therewith;
   the impotence is caused by severe atherosclerosis; and
   the induced erection is sufficient for vaginal penetration.

14. The composition of claim 13, wherein the amount of the neuropeptide is between 15 μg and 60 μg.

15. The composition of claim 14, wherein the neuropeptide is VIP.

16. A composition according to claim 14 wherein the neuropeptide is PHM.

17. The composition of claim 15, wherein said alpha-adrenergic blocker is selected from the group consisting of phentolamine, at a concentration of between 2 μg/ml and 20 mg/ml and prazosin, at a concentration of between 2 µg/ml and 10 mg/ml.

18. The composition of claim 16, wherein said alpha-adrenergic blocker is selected from the group consisting of phentolamine, at a concentration of between 2 µg/ml and 20 mg/ml and prazosin, at a concentration of between 2 µg/ml and 10 mg/ml.

19. A composition according to claim 17 wherein said alpha-adrenergic blocker is phentolamine.

20. A composition according to claim 18 wherein said alpha-adrenergic blocker is phentolamine.

21. A composition that is physiologically acceptable for administration to a human male by intracavernosal injection, consisting essentially of:
 (a) 5–500 µg/ml of vasoactive intestinal peptide (VIP) peptide or histidine methionine (PHM); and
 (b) 20 µg/ml–20 mg/ml of phentolamine in a physiologically acceptable solution.

* * * * *